United States Patent
Quinn

(10) Patent No.: US 8,298,496 B2
(45) Date of Patent: Oct. 30, 2012

(54) FLUIDIC CONFIGURATION FOR FLOW INJECTION ANALYSIS

(75) Inventor: John Gerard Quinn, Edmond, OK (US)

(73) Assignee: FLIR Systems, Inc., Wilsonville, OR (US)

( * ) Notice: Subject to any disclaimer, the term of this patent is extended or adjusted under 35 U.S.C. 154(b) by 77 days.

(21) Appl. No.: 12/670,078

(22) PCT Filed: Jan. 16, 2008

(86) PCT No.: PCT/US2008/000515
§ 371 (c)(1),
(2), (4) Date: Jan. 21, 2010

(87) PCT Pub. No.: WO2009/014553
PCT Pub. Date: Jan. 29, 2009

(65) Prior Publication Data
US 2010/0196205 A1    Aug. 5, 2010

(51) Int. Cl.
*G01N 15/06* (2006.01)
*G01N 33/00* (2006.01)
*G01N 33/48* (2006.01)

(52) U.S. Cl. ......... 422/503; 422/68.1; 422/50; 422/400; 422/401; 422/81; 422/82.05; 422/502; 422/504; 436/43; 436/63

(58) Field of Classification Search ............... 422/68.1, 422/50, 400, 401, 402, 81, 82.05, 502, 503, 422/504, 509; 436/43, 63
See application file for complete search history.

(56) References Cited

U.S. PATENT DOCUMENTS

| | | | |
|---|---|---|---|
| 5,313,264 A | 5/1994 | Ivarsson et al. | |
| 5,376,252 A | 12/1994 | Ekstrom et al. | |
| 5,912,456 A | 6/1999 | Melendez et al. | |
| 6,200,814 B1 | 3/2001 | Malmqvist et al. | |
| 6,375,871 B1 | 4/2002 | Bentsen et al. | |
| 6,506,609 B1 * | 1/2003 | Wada et al. ................... | 436/148 |
| 6,645,432 B1 * | 11/2003 | Anderson et al. ............. | 422/502 |
| 6,987,897 B2 * | 1/2006 | Elster et al. ..................... | 385/12 |
| 7,344,681 B1 * | 3/2008 | Fiechtner et al. ............. | 422/504 |
| 2002/0182631 A1 | 12/2002 | Schurmann-Mader et al. | |
| 2003/0007898 A1 * | 1/2003 | Bohm et al. .................. | 422/100 |
| 2003/0022388 A1 | 1/2003 | Roos et al. | |

FOREIGN PATENT DOCUMENTS

| | | |
|---|---|---|
| WO | WO9427137 | 11/1994 |
| WO | WO9610178 | 4/1996 |
| WO | WO9635940 | 11/1996 |
| WO | WO9701087 | 1/1997 |
| WO | WO9936766 | 7/1999 |
| WO | WO03102580 | 12/2003 |

* cited by examiner

*Primary Examiner* — Brian J Sines
(74) *Attorney, Agent, or Firm* — McAfee & Taft

(57) ABSTRACT

A fluidic configuration, both structural and methodological, for the injection of sample greatly reduces dead volume allowing rapid transition to 100% sample in a flow cell. For a continuous flow injection analysis system the structure and method provide counter flows to remove in one direction the dispersed region of the sample to waste before injecting non-dispersed sample into the flow cell by reversing the effective flow direction. The injection point itself is directly adjacent to the flow cell where all channels are microfluidic channels. Therefore, only the flow cell volume needs to be displaced during injection of sample in order to achieve 100% transition to sample within the flow cell. This greatly accelerates the rise and fall times thereby extending the kinetic range of the real-time interaction analysis instrument. In addition such rapid transition to sample improves overall data quality thereby improving kinetic model fitting.

5 Claims, 4 Drawing Sheets

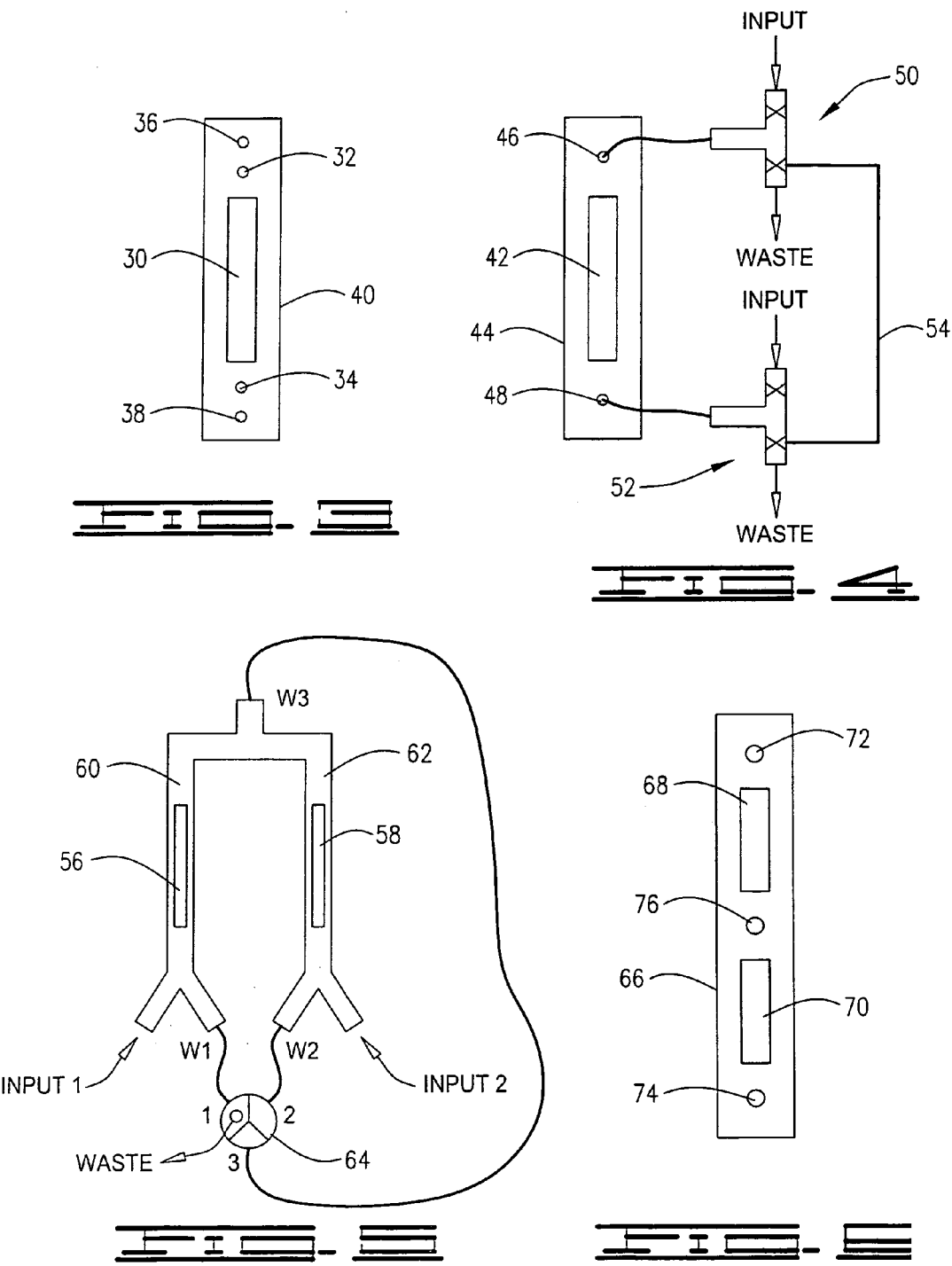

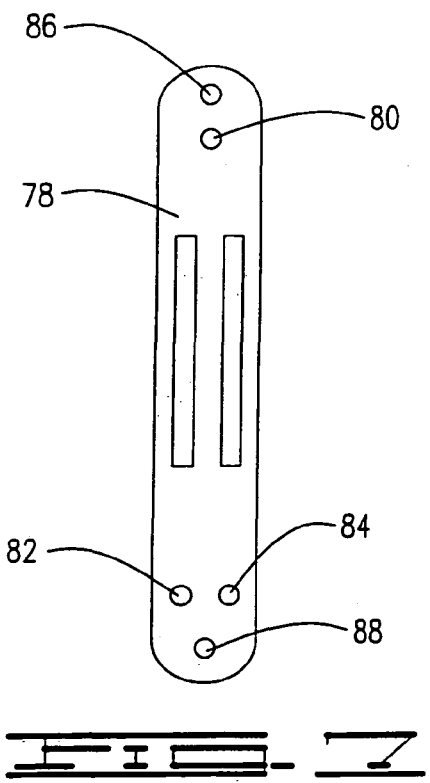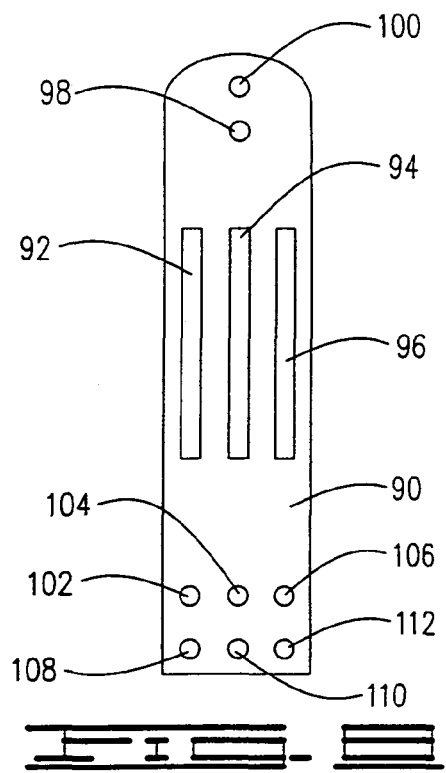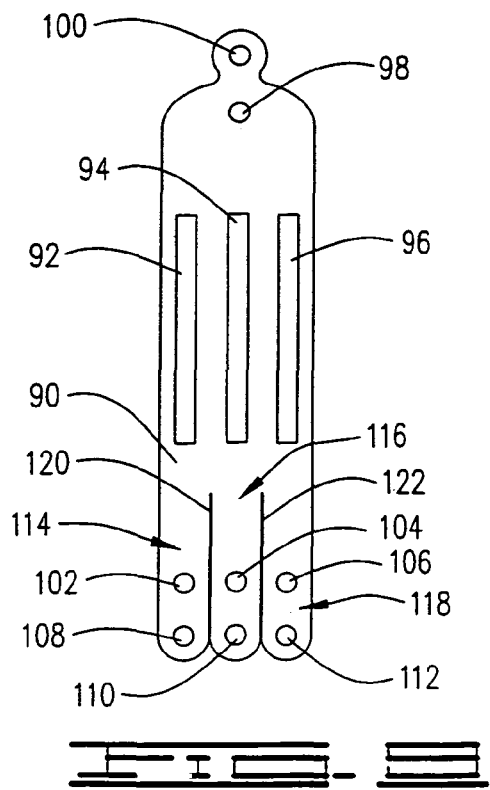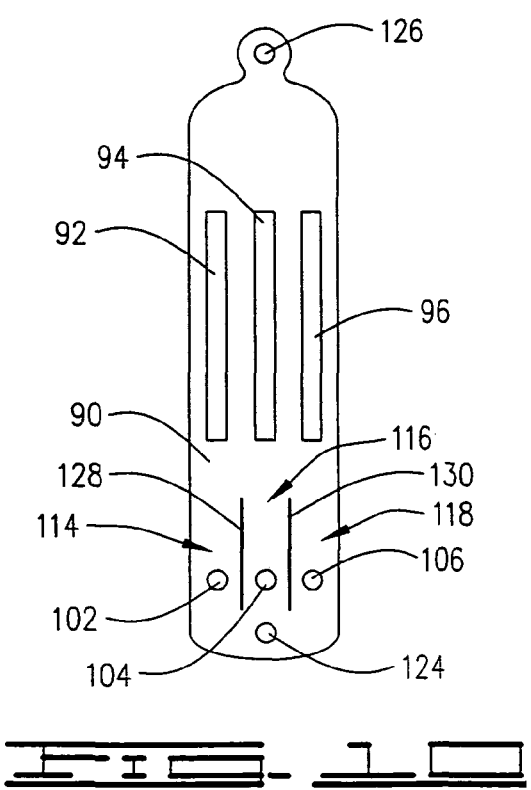

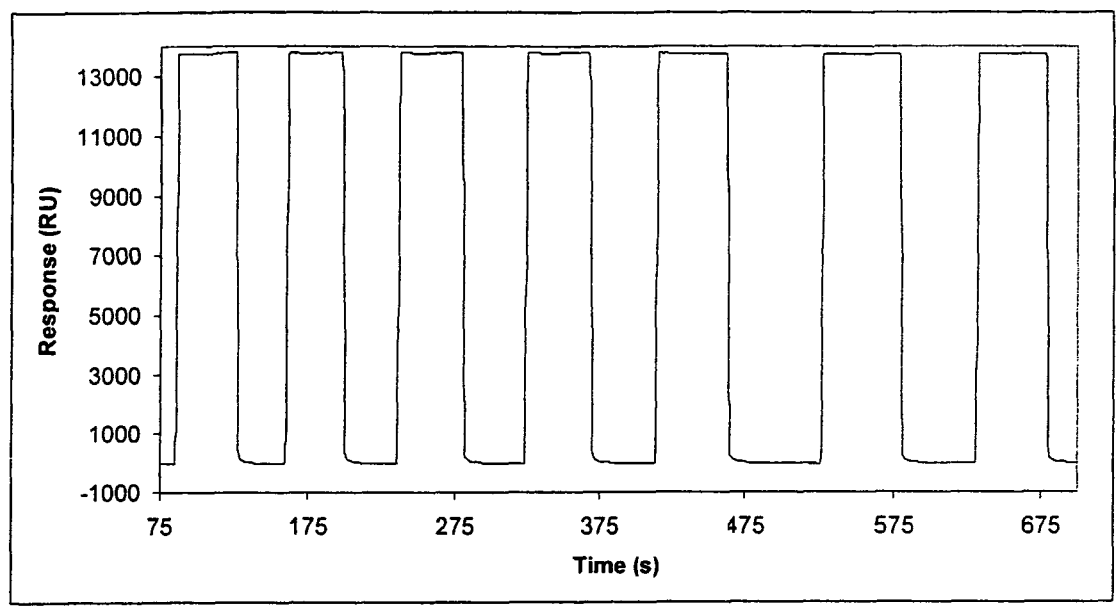
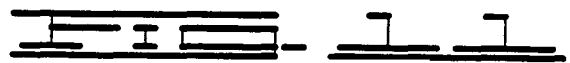

FLUIDIC CONFIGURATION FOR FLOW INJECTION ANALYSIS

FIELD OF THE INVENTION

The present invention relates to fluidic systems and methods with which to inject flows of fluids relative to sensing regions. One particular field of application is microfluidic biosensing using biomolecular ligands and analytes.

BACKGROUND OF THE INVENTION

Analytical instruments such as biosensors are well established as a means of recording the progress of biomolecular interactions in real time. Biosensors are analytical instruments that employ a variety of transduction technologies in order to detect interactions between biomolecules. Such instrumentation requires microfluidic channels in order to deliver samples to a sensing region. Pumps and valves are preferred to provide a means of moving sample through the channels in a controlled reproducible manner.

Recent interest in microfluidics technology has come about because of a growing need for sophisticated control of fluid streams for such sensing applications. A number of prior systems, referred to as integrated microfluidic cards, are composed of a series of substantially planar substrates possessing channels and structures that when bonded form internal passages and active components such as valves and pumps. Despite much progress these systems are rarely as robust as conventional flow injection analysis fluidic systems where the active components are not integrated into the fluidic card; however, these non-integrated systems typically have relatively large dead volumes.

There are several transducers capable of recording the progress of biomolecular interactions, for example a quartz crystal microbalance. Binding of molecules to the surface of a quartz crystal changes the fundamental resonance frequency which allows quantification of the binding event. Other technologies include light scattering, reflectometric interference spectroscopy, ellipsometry, fluorescence spectroscopy, calorimetry, and evanescent field based optical detection. A particularly effective evanescent field based technology, known as surface plasmon resonance (SPR), exploits the behavior of light upon reflection from a gold-coated optical substrate, for example.

SPR is an optical technique that enables real-time monitoring of changes in the refractive index of a thin film close to the sensing surface where materials to be tested are located (typical material types include a ligand attached to the sensing surface, a fluid buffer, and a fluid analyte which is contained (e.g. soluble or insoluble colloidal solution) in a running/flowing material that is to bind with the ligand and be tested). The evanescent field created at the surface decays exponentially from the surface and falls to one third of its maximum intensity at approximately 300 nanometers (nm) from the surface. Hence the SPR technique is sensitive to surface refractive index changes.

An integrally-formed miniature SPR transducer has been described in U.S. Pat. No. 5,912,456. In this device a photodiode array (PDA) simply records the intensity of the reflected light, from a light emitting diode (LED) over a range of angles. Refractive index changes within the penetration depth of the evanescent field give rise to corresponding changes in the position of the SPR reflectance minimum incident on pixels of the PDA. This change in resonance angle is followed by tracking the change in the pixel position of the reflectance minimum. A minimum tracking algorithm is employed to continuously monitor the position of this minimum as it traverses the photodiode array and the pixel position is then related to a refractive index value. A current configuration of this device possesses three SPR active sensing regions per sensor enabling multichannel operation with real-time reference subtraction. Alternative configurations can allow even more numerous SPR sensing regions.

The delivery of samples to the SPR active sensing regions is made possible by creating flow channels that cover the active sensing regions. Each flow channel possesses an inlet and outlet to allow for the flow of buffer, or samples, over the SPR active sensing regions. The thin film sensing surface is derivatized to possess a polymeric coating that enables biomolecules ("ligands") to be permanently immobilized on the coating. The immobilized biomolecules usually possess binding specificity for another biomolecule contained in the sample (the "analyte"). The strength of this binding is given by the affinity constant which is simply the ratio of the binding rate constant divided by the dissociation rate constant. It is possible to measure these constants because an SPR-based biosensor records the progress of binding and dissociation events in real time.

Scaling down biochemical analysis instruments has important advantages (for example, sample volume reduction, microfluidics for high mass transport, and mass manufacturable). As a particular example, U.S. Pat. No. 5,376,252 discloses planar microfluidic structures useful for capillary electrophoresis. The channels of these microfluidic structures may have diameters in the range of 50-250 micrometers (μm) and may be manufactured by molding trenches into the surface of a first thermoplastic base and then clamping a second base to the first base which thereby covers the trenches to form channels.

Similarly, U.S. Pat. No. 6,375,871 discloses a method of manufacturing microfluidic devices by attaching two layers with a molded channel pattern in one layer.

An integrally-formed miniature SPR transducer as described in U.S. Pat. No. 5,912,456 is a disposable element. Such a sensor includes a flow channel block that forms a reversible leak tight seal with the sensor's SPR active sensing regions. Permanent attachment of a flow channel to the SPR active sensing region is possible but this can be difficult to achieve without damaging the surface chemistry attached to the active sensing region. Damage can occur due to chemical and/or mechanical damage during the flow channel attachment process. In addition, making reliable, and reversible, fluid connections with the flow channel inputs is difficult.

There are many factors that can have a significant influence on the performance of a biosensor and the quality of the analytical data recorded. Of particular importance are the flow channel's physical properties. Indeed, for an SPR-type sensor the SPR signal is averaged over the SPR active area, and the transport of the biomolecule of interest (analyte) contained in the sample to the SPR active surface results from convective and diffusion forces. These phenomena are described by the mass transfer coefficient ($k_m$) and are related to the flow channel dimensions and operational flow rate according to the following expression:

$$k_m = C \sqrt[3]{\frac{D^2 F}{h^2 w l}} \tag{1}$$

where
D=Diffusion coefficient of the analyte (m²/s)
h, w, l=Height, width, and length of flow channel (m)

Bulk flow rate (μl/min)
C=Constant

Typical kinetic analysis of biomolecular interactions requires that a stable analyte concentration gradient exists and this requires laminar flow conditions. Flow channels with heights that exceed 0.5 millimeter (mm) (500 μm) are often characterized by non-laminar flow conditions. Turbulent flow conditions must be avoided if analytical reproducibility is required. It is apparent from equation (1) that mass transport rates are greatly influenced by the size of the flow channel (particularly the flow channel height) and this has a large effect on the magnitude of binding signals that may be detected. Thus effort should be made to ensure that the flow channel dimensions are minimized. In addition, miniaturization of the flow channel dimensions will ensure that mass transport rates are high. If mass transport rates are low, as is the case with large flow channels, then medium to fast kinetic interaction data will represent mass transport rates and not the kinetic constants for the interaction. This is particularly true when the binding rate of the analyte to the immobilized biomolecule (i.e., ligand) is high.

There is a practical limit to the miniaturization of the flow channel dimensions and this is dictated by considerations of contact area, backpressure, and fluid dynamics, as follows.

Flow Channel Contact Area:

The smaller the flow channel area in contact with the sensing surface, the greater the binding response recorded. If the flow channel area in contact with the sensing surface increases, then the ligand binding response will decrease. This is intuitive as the same number of bound molecules are averaged out over a greater area. The SPR signal records the averaged mass increase per unit area.

Backpressure:

The theoretical flow resistance, R, in a rectangular channel, with a high aspect ratio (i.e., the width is far greater than the height), can be estimated from the Poiseuille slot flow equation where, $$R = \frac{12\mu L}{wh^3} \quad (2)$$

where
  μ=Solution viscosity
  L=Length of channel (i.e., flow channel)
  w=Width of channel
  h=Height of channel The backpressure scales inversely according to the cubic power of the channel height. This shows that decreasing the flow channel height by 2-fold will give an 8-fold increase in resistance to flow. If the resistance is high, then the flow channel seal must be leak-proof above that pressure. Therefore, flow channel heights below 15 μm are not practical for low pressure systems. In addition, flow channels below this height are easily blocked by particulates that are often present in unfiltered samples and buffers. In addition, the internal diameter of tubing used to deliver sample to each flow channel should be greater than 50 μm in order to avoid excess backpressure as backpressure scales inversely according to the sixth power of the radius in tubular channels. In addition excess backpressure causes delays in reaching a steady-state flow. Such delays have significant effects on the performance of the biosensor system. In particular, the time required for a full exchange of running buffer with sample within each SPR flow channel will be delayed. If a bulk refractive index variation exists between the running buffer and sample, then the response due to this bulk index response is difficult to resolve from the actual binding signal, without using a reference channel, unless the exchange time can be reduced (i.e., to less than 10 seconds).

General Fluidic Dynamics Design Principles and Gradients:

A vertical gradient from flow through a vertically oriented small channel is described by a parabolic flow profile where the velocity of the liquid at the walls is zero and the velocity is maximal towards the center of the channel. These velocity gradients cause uneven distribution of analyte binding at the surface. In particular it is important that the SPR active surface is not positioned near the wall of the flow channel where the velocity, and hence analyte binding, is very low. Turbulent flow will exist at the inlet and outlet causing unpredictable analyte binding. Therefore, the SPR active region should be centered along the middle of the flow channel, thereby separating the active sensing regions from the walls, and the inlet/outlet holes.

Also, due to the transit/displacement time through the sensing region of the flow cell, an analyte binding gradient might be caused to exist when a sample is injected into a flow cell. As sample flows into the sensing region, the sample displaces the liquid that is already there. Typically this is a displacement in the direction of flow. Depending on the volume of this region of flow and the flow rate, this displacement may require significant time to carry analyte in the sample across the sensing region. This will cause a gradient in analyte binding to exist along the sensing region in the direction of flow. This gradient can be difficult to account for when processing the data obtained from the flow cell. In some cases it is assumed that this gradient does not exist, but this assumption is only true if the time for complete displacement of the liquid in the flow cell is sufficiently short (e.g., less than one second). For example, if the flow cell volume is 50 nanoliters (nL) and the sample is injected at 50 microliters (μL)/minute, then the flow cell volume is displaced 1,000 times per minute or about 16.6 times per second. The analyte gradient along the flow cell may be neglected in this example. However, if the flow cell volume is 50 μL, then at a flow rate of 50 μL/minute the flow cell is displaced only once each minute, which cannot be neglected.

U.S. Pat. No. 5,376,252 and U.S. Pat. No. 5,313,264 disclose fabricating miniature valves that may be completely integrated into a microfluidic path thereby decreasing prechannel dead volume, which is the volume between the injection point and the flow cell sensing region. This type of dead volume influences the rise and fall times of responses to the sample when it is injected into the flow cell. Accordingly, it is preferable to minimize prechannel dead volume.

Another type of dead volume, interchannel dead volume, typically exists between two sensing channels. This type of dead volume can cause distortions when performing reference curve subtraction and so interchannel dead volume preferably should be minimized. Dead volume between two sensing channels affects the arrival time of sample at the second flow channel. Ideally sample should contact both sensing channels simultaneously if accurate reference curve subtraction is required. A time delay between channels may be accounted for during processing; however, the additional dispersion that occurs in this interchannel dead volume can give rise to response variations between channels if any bulk refractive index difference exists between the sample and the running buffer. In practice such bulk refractive index differences can be expected and reference curve subtraction will therefore introduce artifacts. Thus, such delays decrease the reproducibility of binding responses from one SPR channel to the next and also make reference subtraction more difficult. So the reduction of dead volumes is critical in ensuring high analytical performance. For example, it is usual to use the data from a reference channel to correct data from a working channel in order to subtract baseline drift, non-specific binding and particularly bulk refractive index changes. This reference subtraction method will not be effective if a large dead volume, and hence significant dispersion, exists between both flow channels. For example, if a device has a dead volume of >0.5 µL between each of four flow cell channels where the flow cells themselves have a volume of about 30-60 nL, the dead volume is as much as 16-fold greater than the flow cell volume. This dead volume must be completely washed out before sample dispersion is no longer present. If we assume that a transition to 95% sample is acceptable, then a wash-out volume of 2.7 times the dead volume is required (note: this dilution process follows a natural logarithm, where e=2.72, hence a volume of sample equal to approximately 2.72 times the dead volume must pass through before the sample concentration reaches about 95% of its actual concentration). Therefore, given a 0.5 µL interchannel dead volume between channels 1 and 2, if performing a binding experiment where the sample is injected at 20 µL/min, the first 1.36 µL of sample entering channel 2 will suffer from dispersion, representing four seconds of data where dispersion differences exist between channels 1 and 2. The dispersion period preferably should be reduced to less than 0.5 seconds in order to measure the kinetic parameters of fast interactions. For example, a very weak interaction will often reach steady state in 1 second or less and dissociation may also occur in less then 1 second. In this case, kinetic resolutions would require reducing the dispersion period to a fraction of second or a fraction of the time of the events to be measured. Thus, a transition of 0.1 to 0.2 seconds is preferable.

Prechannel dead volumes that exist in the flow path before reaching the flow cell will cause dispersion that occurs equally in both channels 1 and 2 and is therefore subtracted during reference curve subtraction. Therefore this is of lesser concern, but it is still advantageous to reduce these dead volumes. If these dead volumes are large, then the injected sample will suffer from dispersion for a considerable portion of the injection. Usually injections of >2 minutes are employed. A prechannel dead volume of about 1 µL will show dispersion for 8 seconds at a flow rate of 20 µL/min. That is about 6.6% of the total injection time assuming a 2 minute injection period. During this 8 second dispersion period the sample concentration will be variable and a similar 8 second dispersion period will occur on ending the injection. These dispersion periods complicate kinetic model fitting to the dispersed regions and should be reduced where possible.

U.S. Pat. No. 6,200,814 describes a means of reducing or eliminating the dispersion due to dead volumes that occur before sample injection and also the interchannel dead volume (see, also, PCT publication WO 03/102580 A1). In the '814 patent the sample is allowed to flow into the flow cell but is prevented from contacting the sensing regions due to the presence of a second, or third, stream of liquid (i.e. running buffer) flowing in the same direction adjacent to the sample stream. Here the non-mixing behavior of parallel flowing laminar flow streams is exploited wherein the sample flow stream is separated from the sensing surface along the flow cell by providing a buffer flow along the sensing region such that a buffer-sample interface extends along the length of the flow cell. In this way the dispersed region is allowed to flow to waste before contacting the sensing area and an effective injection point is moved into the flow cell itself. By changing the relative flow rates between these adjacent laminar flow streams, the sample stream is forced to make a rapid lateral displacement allowing a rapid (<0.3 seconds) transition from running buffer to 100% sample over the chosen sensing area. This method is critically dependent on the non-mixing behavior of laminar flow streams. Any disruptions caused by bubbles will prevent normal operation making the system less robust, requiring expensive degassing devices. Furthermore a means of controlling the flow rate in multiple streams adds additional pump drives that introduce considerable expense.

SUMMARY OF INVENTION

A fluidic configuration, both structural and methodological, for the injection of sample greatly reduces dead volume allowing rapid transition to 100% sample in a flow cell. For a continuous flow injection analysis system the structure and method provide counter flows to remove in one direction the dispersed region of the sample to waste before injecting non-dispersed sample into the flow cell by reversing the effective flow direction. The injection point itself is coplanar with the sensing surface and directly adjacent to the flow cell where all channels are microfluidic channels. Therefore, only the flow cell volume needs to be displaced during injection of sample in order to achieve 100% transition to sample within the flow cell. This greatly accelerates the rise and fall times thereby extending the kinetic range of the real-time interaction analysis instrument. In addition such rapid transition to sample improves overall data quality thereby improving kinetic model fitting.

Therefore from the foregoing, it is a general object of the present invention to provide a novel and improved fluidic configuration (both apparatus and method) for a flow injection analysis system. A particular object relates these to biosensing. Other and further objects, features, definitions, and advantages of the present invention will be readily apparent to those skilled in the art when the following description of the preferred embodiments is read in conjunction with the accompanying drawings.

BRIEF DESCRIPTION OF THE DRAWINGS

FIG. 3 schematically illustrates another embodiment of a single channel, single sensing region flow cell of the present invention.

FIG. 4 schematically illustrates a further embodiment of a single channel, single sensing region flow cell of the present invention.

FIG. 5 schematically illustrates an embodiment of a double channel, double sensing region flow cell of the present invention.

FIG. 6 schematically illustrates an embodiment of a single channel, double sensing region flow cell of the present invention.

FIG. 7 schematically illustrates another embodiment of a single channel, double sensing region flow cell of the present invention.

FIG. 8 schematically illustrates an embodiment of a single channel, triple sensing region flow cell of the present invention.

FIG. 9 schematically illustrates another embodiment of a single channel, triple sensing region flow cell of the present invention.

FIG. 10 schematically illustrates still another embodiment of a single channel, triple sensing region flow cell of the present invention.

FIG. 11 graphically illustrates sensor response plotted as a function of time corresponding to the example configured in accordance with a preferred embodiment (seven sequential injections of sample with increasing flow rates from 5 μL/min to 100 μL/min).

DETAILED DISCLOSURE OF THE INVENTION

Figure 1:
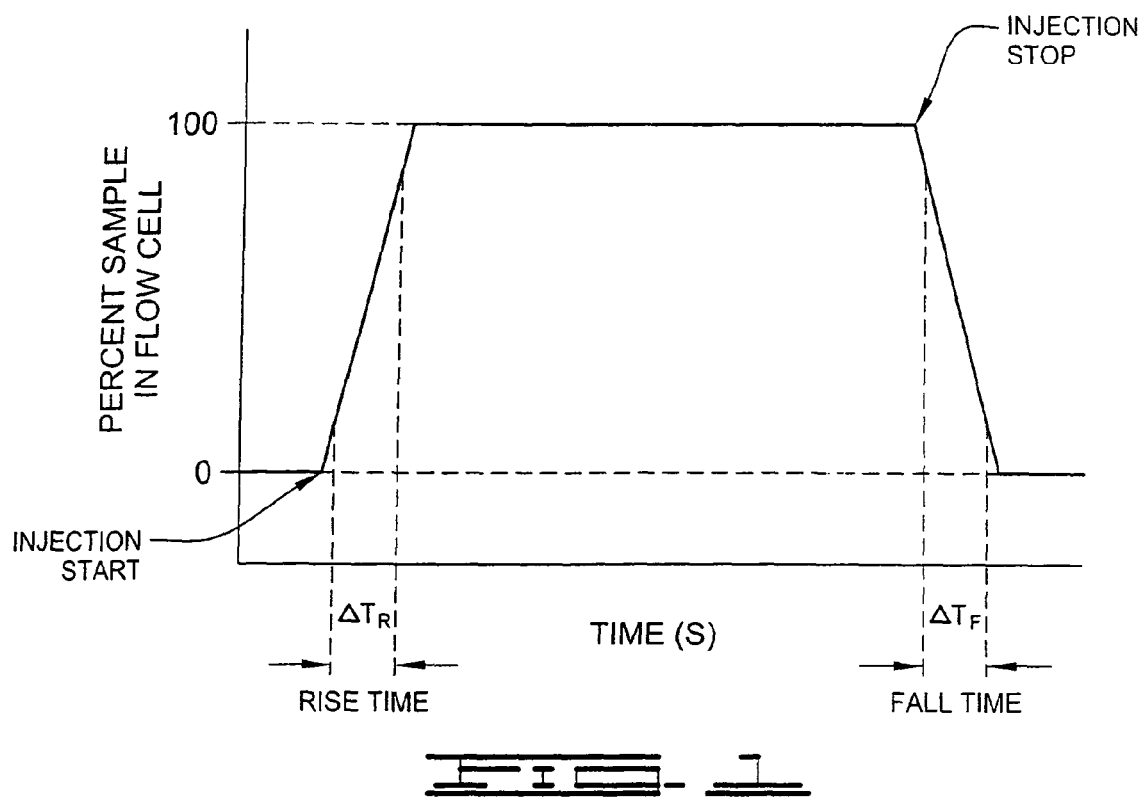
FIG. 1 is a graph representing the relative fraction of sample in the sensor flow cell during a sample injection.

The following detailed explanation describes particular novel and improved injection method and structure that eliminate significant dead volume. "Significant" as used here and in any appended claims means that a dead volume may exist, but any such dead volume is so small that the sample transits the sensing area in a time, shorter than binding or dissociation events can be measured between components of the sample fluid and components bound to the sensing area. Thus, in the present invention an injection of sample approaches 100% sample inside the flow cell within one second. This is accomplished without requiring integrated microfluidic valves, laterally displaceable parallel laminar flow streams, or multiple pump drives. A biosensor for real-time biomolecular interaction analysis is one type of application for the present method and structure.

In one implementation as a microfluidic flow channel device a stream selector valve selects only one, of two or more, waste ports at any one time. This selector valve is not integrated into the microfluidic device but is connected by standard tubing and fittings. In addition, a counter flow of liquid opposing the flow of the sample into the flow channel sensing area prevents the early dispersed region of the sample from contacting the sensing surface(s) because the dispersed region of the sample is forced to flow to waste in the opposite direction to the sensing area. Once the dispersed region of the sample has been sent to waste, then the remainder of the sample is injected over the sensing area by simply reversing the flow direction by switching to the waste output at the opposite end of the flow channel(s). In this configuration the injection point is preferably coplanar with the sensing surface(s) and is at the intersection of the sample input and countering flow near the dispersed sample waste port. This intersection is preferably coplanar with and can be placed very close to the sensing area. Therefore using this approach the dead volume to be displaced is the volume of the flow cell itself. This volume may be very low (e.g. 5-100 nL). Multiple sensing regions may be positioned serially along the length, or laterally, across the width of the flow channel but parallel to the fixed longitudinal direction of sample flow.

In a preferred application the flow injection analysis system is a biosensor system for measuring association (binding) and dissociation (unbinding) reactions between an immobilized biomolecule ("ligand") and a soluble biomolecule ("analyte"). The fluidic system and method enhance the performance of the biosensor system while eliminating the need for expensive integrated microfluidic cards and multiple pump drives. In particular the reduction in dead volumes that is achievable using this fluidic system is possible while using conventional off-the-shelf valves and pumps. Specific purpose-designed components can be readily machined on modern computerized numerical control (CNC) machines, for example.

The detrimental dispersion, or dead volume (or zone), referred to above places a limit on the range of association and dissociation interactions that can be analyzed. For example, weak interactions can reach a steady state very quickly (e.g. 2-3 seconds). An 8-second dispersion period, for example, as referred to above prohibits accurate binding response measurements and mathematical model fitting to the association phase for determination of the association rate constant because the binding occurs before the dispersed zone passes where both the concentration of analyte and the bulk refractive index are variable. In addition the analyte may dissociate completely in less than 8 seconds making it difficult to determine the dissociation rate constant. Decreasing the dispersion period would allow these fast interaction events to be recorded where both the analyte concentration and bulk refractive index are substantially constant throughout the injection as is assumed in kinetic model fitting. FIG. 1 illustrates how this dispersion time may be considered. In this plot the fraction of sample contained in the flow cell during an injection is represented. Ideally the transition to 100% sample should be instantaneous. Equally the transition back to 0% sample at the end of injection should be instantaneous. In practice this is difficult to achieve because of dispersion as explained above. The time to reach 100% sample is referred to as the rise time. For the purpose of calculation, however, it is sufficient to consider the rise time as being the time required to change from 5% sample to 95% sample. Other definitions may be applied.

A plot of the percentage of sample in the flow cell as a function of time is shown in FIG. 1. Assume that the injected sample reaches 100%. In an ideal experiment the sensor response should transition from a 100% running buffer response to a 100% sample response infinitely fast. In practice this transition requires a finite time that is a function of the dead volume between the flow cell (specifically the sensing area thereof) and the locus of injection. This dispersion time is often referred to as the rise/fall time. If the prechannel dead volume is very high, then it is possible that the sensor response will never approach 100% sample during an injection. In FIG. 1 there is a short delay relative to the injection start time. The rise/fall times are sometimes estimated at the 98% transition. Here we approximate the rise/fall times as the times required to transition between 5% and 95% of the maximum. As discussed above, eliminating any volumes between the point of sample injection and the flow cell enables rapid rise/fall times. The present invention successfully achieves this by employing counter flowing streams.

To overcome this dead volume problem, the new injection method and apparatus of the present invention will first be described for a single channel sensing system; however, the approach is easily scalable from one to many channels.

Figure 2:
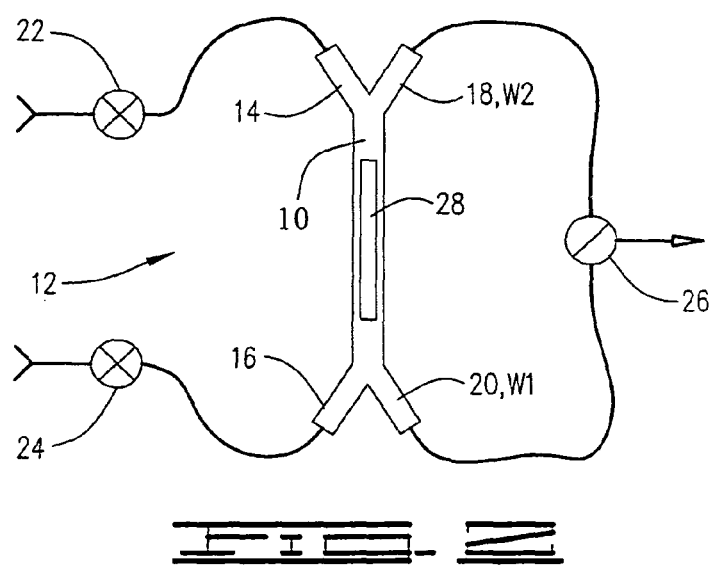
FIG. 2 schematically illustrates an embodiment of a single channel, single sensing region flow cell of the present invention.

FIG. 2 represents a flow channel conduit 10 of a flow cell 12 with two inlet ports 14, 16 and two outlet ports 18, 20 in accordance with the present invention. Each inlet port 14, 16 is connected to a two-position valve 22, 24, respectively, allowing flow of buffer or sample. The two outlet ports 18, 20 (also referred to herein as "wastes"—here port 18 is waste 2, or W2, and port 20 is waste 1, or W1) are connected to waste selector valve 26. In a preferred embodiment only one waste is open at any time. The flow of sample is controlled as follows.

With waste 2 closed, buffer input through inlet port 14 flows to waste 1, which is open. Once buffer flow from its input to waste 1 occurs, then simultaneously with continued buffer flow, sample flows in from inlet port 16 and exits at waste 1 thereby preventing the dispersed portion of the sample from contacting a sensing surface 28 in flow channel 10. The leading edge of the sample injected from inlet port 16 will suffer dispersion due to mixing with buffer present in the fluidic line before arrival of sample. This dispersion volume is conveniently eliminated by allowing this volume to run to waste 1. Sample cannot enter the longitudinal flow channel 10 because of the counter-flowing buffer from inlet port 14. Once this dispersed sample volume is eliminated, however, the remainder of the sample may be injected into the flow cell by switching the valve 26 to open waste 2 and close waste 1. A rapid vertical (for the upright orientation illustrated in the drawing) displacement of the buffer in the flow cell will be effected. Thus the effective injection point is at the intersection of inlet port 16 with outlet port 20 where the two flows of buffer and sample meet. The only dead volume left is therefore the volume of the longitudinal flow channel (nL scale, e.g. 50 nL) itself, thereby allowing a rapid rise time. Similarly a rapid fall time is obtained by again switching wastes. This would be done before the tailing edge of the sample arrives as this will also suffer dispersion. Flow of buffer from inlet port 14 to waste 2 during a sample injection is optional. Both ends of the flow channel are symmetrical thereby allowing the sample injection to be performed from either input and with the same rapid rise/fall method.

As used for input and output of buffer and sample fluids, the ports of the present invention can be referred to as buffer port means and sample port means. These provide means for enabling the flow of the buffer fluid along the conduit and sensing area from the buffer port means to the sample port means simultaneously with a flow of sample fluid through the sample port means such that a dispersed portion of the sample fluid exits the flow cell (such as for a biosensor) without contacting the sensing area (such as specifically ligands attached in the sensing area) and for thereafter longitudinally flowing the sample fluid through the conduit such that at least a portion of the non-dispersed sample fluid (such as specifically analyte of the sample fluid) contacts the sensing area (such as specifically the ligands) and the sample fluid displaces buffer fluid out of the conduit through the buffer port means.

The ports and connected valves of FIG. 2 are one implementation of means for bidirectionally flowing a first fluid and a second fluid in opposing first and second directions in the flow channel conduit such that in the first direction a first fluid flows over the sensing area and removes at least a portion of a second fluid from the flow channel conduit and in the second direction the second fluid flows over the sensing area and removes the first fluid from the sensing area of the flow channel conduit. Although not expressly depicted in each drawing, suitable flow control components and circuitry are used with the implementations described herein as needed for effecting the methods and apparatus of the present invention.

The flow channel conduit system described in FIG. 2 may take a variety of forms. One is represented in FIG. 3. The flow channel structure in FIG. 3 is equivalent in functionality to that of FIG. 2. A sensing region 30 is bounded at either end by inlet ports 32, 34 and outlet ports 36, 38 as in FIG. 2. However in this case all ports are bound within a linear channel 40 with no intersecting branches as in FIG. 2.

FIG. 4 illustrates that the respective inlet and outlet ports can be implemented using common ports, or openings, in the body of the flow cell. As a variation of the FIG. 3 structure, the FIG. 4 structure includes a sensing area 42 in a longitudinal conduit 44 with openings 46, 48 off opposite ends of the sensing area 42. Flow control is achieved with external valves and couplings 50, 52. As throughout the illustrated embodiments of the present invention, some type of control of the waste outlet ports is used so that only one waste is open at a time to achieve the bidirectional, insignificant dead volume flows of the present invention. Such control can be by whatever means is suitable for a given situation and application. The interrelationship of waste port control is simply illustrated in FIG. 4 by line 54.

A preferred implementation of this injection method and fluidic configuration employs a dual channel surface plasmon resonance based biosensor. The injection method and apparatus of the present invention can be adapted to a dual channel system as shown in FIG. 5. Again only a single waste can be open at any time. In this case the sample is injected over both sensing surfaces 56, 58 disposed in respective, but commonly connected, flow channels 60, 62 (the interconnecting section between the flow channels is preferably small, such as on the order of 20 nL). Ports defining fluid inputs (inputs 1 and 2) and waste outputs (W1 and W2) are at the free ends of these channels.

For example, to perform a sample fluid injection from input 1 the following sequence is performed. Buffer enters input 2 with waste 1 open. Therefore the buffer is flowing anti-(or counter-)clockwise (as viewed in FIG. 5) through both flow cells. Sample fluid entering input 1 also exits waste 1 until the dispersed zone is run to waste. Waste 2 is then opened thereby closing waste 1 thus causing a rapid transition from 100% buffer to 100% sample in both flow cells. Thus the injection is controlled by switching the waste valve position if a single valve is used to control the open or closed state of the waste ports 1 and 2. Both left and right sides of this dual channel design are symmetrical allowing the injection to be performed in an identical fashion from input 2. Waste 3 is optional but is desirable because using it enables the sample to be flowed through a single channel.

Flow through the waste lines is controlled at a distance by connecting fluid lines to the waste ports. For example, a multichannel stream selector valve 64 may be connected to the three waste ports W1, W2, W3. This selector valve may be actuated to respective actuation positions to open the desired waste stream while dead ending all others (in the illustration of FIG. 5, actuation position 1 is shown with W1 open to the waste opening of the valve 64 and with W2 and W3 dead ended; valve actuation position 2 opens W2 and closes W1 and W3; and actuation position 3 opens W3 and closed W1 and W2). The waste selector valve 64 should switch rapidly to prevent pressure surges while the waste selector valve 64 is actuating. This valve and the inlet flow control component(s) provide one implementation of means for controlling longitudinal flow through one or more flow channels so as to enable simultaneous input flow through inlet ports but sequential output flow through outlet ports such that a single outlet port is open at any one time thereby reversibly controlling the direction of flow over the sensing area by switching between the outlet ports. Considering two outlet ports, in response to an open second outlet port and closed first outlet port a sample fluid entering its inlet port is made to flow to the second outlet port due to flow of a second fluid entering through its inlet port, but sample fluid injection over the sensing area is brought about by switching the outlet ports such that all flows are directed to an open first outlet port and away from a closed second outlet port.

Although the flow channels 60, 62 of the FIG. 5 implementation are geometrically pictured as parallel, the flow within the channels is in series, extending between the input/waste 1 end to the input/waste 2 end. Such serial flow/sensing region relationship can be achieved with other geometries. One such example is shown in FIG. 6 with a single longitudinal structure including flow conduit 66 with serially disposed sensing regions 68, 70 in it. Separate or combined ports or combinations thereof can be used in this, as well as the other, configurations of the present invention. In FIG. 6 there is porting 72

(such as for input 1 and waste 1 in reference to FIG. 5) off one end of the sensing regions 68, 70 and porting 74 (such as for input 2 and waste 2 in relation to FIG. 5) off the other end of the sensing regions. Optional intermediate porting 76 (such as for W3 in relation to FIG. 5) is also shown. Also, the sensing region(s) may be very short, or even a spot, in which case the sensing region(s) may be perpendicular or diagonal to the flow of fluid.

FIG. 7 shows a version of the flow conduit system with the sensing regions adjacent to, but separate from, each other and not in series along the channel. The conduit system here includes a single flow channel 78 with multiple inlet ports 80, 82, 84 and two outlet ports 86, 88. This conduit system can be used for a low dispersion injection of a sample over multiple sensing regions or injection of multiple samples over multiple sensing regions.

FIG. 7 shows the flow conduit system for a system with two sensing regions and FIG. 8 represents a flow conduit system for a system with three sensing regions. FIG. 8 is shown as comprising a flow channel 90, parallel laterally spaced sensing regions 92, 94, 96, buffer inlet port 98, outlet port 100, sample inlet ports 102, 104, 106 and respective adjacent outlet ports 108, 110, 112. Note that each sensing region possesses an associated inlet port, each such port aligned longitudinally with the respective sensing region. Regarding the outlet ports, there can be individual respective ones (as in FIG. 8) or common ones (as in FIG. 7). Regardless of the particular configuration, the injection of sample does not require lateral displacement of adjacent laminar flow streams. Again only a longitudinal displacement of sample is used.

By using only longitudinal displacement in the direction of flow, the flow channel conduit systems, whether with single, series, or parallel sensing regions, may be operated using a single pump drive. Referring to the flow cell of FIG. 8, for example, a single-drive multiple syringe pump that supports four syringes would be sufficient as a single flow rate is allowed through input ports 1, 2, and 3 (102, 104, 106). Ideally the fourth syringe should possess a larger volume to support a higher flow rate through the buffer input port 98. For example, the flow of buffer through the buffer input port may be controlled by a 1-2 nL syringe while the flow through the remaining input ports may be controlled by 0.25-0.5 nL syringes. The operation of this multiple sensing area version is identical to those described earlier but this design also enables individual sensing areas to be exposed longitudinally to sample. The operation of this system does not require on-the-fly focusing of sample injections by using adjacent laminar flow streams that are varied as the sample injection progresses. Instead, in the present invention which sample stream is to flow over which sensing region(s) is predetermined and set prior to injection; once injection occurs, those pre-established adjacent flows are injected, thereby resulting in longitudinal fluid displacement relative to the sensing region(s) without mid-injection lateral displacement change to another sensing region. Thus, the operation of the system does not use lateral displacement changes of adjacent laminar flow streams during injection, rather only longitudinal flows fixed throughout the length of the flow channel are used (i.e. once a sample flow is established relative to a sensing region, such flow is not shifted laterally—it follows its fixed longitudinal path along the length of the sensing region).

The operation of a multi-channel system will be described with reference to FIG. 8.

Fluid (e.g. usually continuous flow buffer) enters from the inlet port 98 and exits at waste (defined through one or more open outlets 108, 110, 112 acting jointly as one common waste output). While the buffer flows, the sample, or samples, or buffer enter from inlet ports 102, 104, 106 and also flow to this waste. In this way the dispersed region of each sample is eliminated to waste. After the dispersed region has been eliminated then the sample(s) are exposed to the sensing areas by opening outlet port 100 and closing ports 108, 110, 112. This causes a reversal of flow along the channel 90 bringing the samples in contact with the sensing surfaces 92, 94, 96 by displacing the fluid from inlet 98 vertically along the channel 90. In FIG. 8 the result is a series of three laminar flow sample streams, each positioned over a respective region of the sensing area. The position of the sensing surfaces and inputs are arranged to allow each of the samples to contact a different sensing area. If a single sample is to be injected over all sensing areas, then flow through the other sample inputs is stopped to allow a single sample stream to fill the entire channel. One of the more significant advantages of this design is allowing the sample to contact two or more sensing surfaces almost simultaneously, thereby avoiding time delays in arrival of sample at a particular sensing area. This improves the data quality making it more amiable to kinetic model fitting.

The shape of the flow channel may be altered to enhance flow characteristics and minimize turbulence when the injection takes place. This turbulence during the start of an injection (e.g. when changing the flow direction) may cause momentary cross-contamination between the sensing channels but this should exist for only an instant followed by a rapid transition to laminar flow (while this cross-contamination is not ideal to have, its duration is short enough that it does not significantly adversely affect the results).

To reduce such cross-contamination, the sample input side of the flow channel can be divided into a series of compartments where one compartment is added for each sensing area. This uses a separate waste port for each compartment as shown in FIG. 9, which shows compartments 114, 116, 118 added by incorporating walls or other barriers 120, 122 into the configuration of FIG. 8 (as understood by the use of like reference numerals in FIG. 9, with geometrical differences for flow channel 90 simply showing that the geometries can be varied while remaining within the scope of the invention). However, more or fewer waste ports could be used. For example, a single commonly shared waste port 124 is shown in the embodiment of FIG. 10. This waste output is accessed around the ends of barriers 128, 130 which do not extend to an end wall of the flow channel as do barriers 120, 122 in the FIG. 9 embodiment. Also depicted in FIG. 10 is a combined inlet/outlet port 126 in lieu of ports 98, 100. Otherwise FIG. 10 shows the same components of FIG. 9. When the injection takes place, the compartments will tend to stabilize the flow from the input ports during the flow directional change. Thus the flow will be a laminar stream when it approaches the sensing areas thereby preventing cross-contamination. Each compartment provides means for preventing mixing of fluids upon entering the flow channel through the compartmentalized inlet ports but for allowing a fluid injected through any such inlet port to contact any sensing region therefrom absent blocking adjacent flow.

It is advantageous to minimize the distance of the input ports to the same-end waste ports and also to minimize the distance of the input ports to the start of the sensing area. A longer compartmentalized region will tend to improve performance by ensuring that the streams are laminar before contacting the sensing areas. However, the additional length required for the compartments will not result in a significant increase in the rise/fall time as long as the volume within each compartment is small (e.g. <100 nL).

It is possible to operate the fluidic systems shown in FIGS. 7-10 where flow through each inlet port is individually controlled. These flows would be set before the injection is performed and would stay constant as the injection is performed. This enables flexible addressing of sample to particular sensing areas. Many variations are possible. For example, with reference to FIG. 9, if sample from input port 102 is to be injected over all three sensing areas, then flow in the other two sample ports 104, 106 is set to zero. Similarly sample from input 104 or 106 may be exposed to all three sensing areas. It is also possible to expose sample only to sensing region 92 by allowing sample flow through inlet port 102 and having sample inputs 104 and 106 deliver running buffer as opposed to sample. It is apparent that sample from sample input port 102 cannot contact sensing region 96 without contacting sensing regions 92 and 94. Similar restrictions hold for other input channel-sensing surface combinations. Sample from input 102 can contact sensing regions 92 and 94 by stopping flow through sample port 104 and allowing a ⅓ fractional volumetric flow rate of buffer through sample port 106. Again these flow rate settings are fixed before the injection takes place and define the fixed longitudinal flow pattern of the various laminar flows in advance of performing the injection.

Therefore in the fluidic system and method of the present invention an injection is performed by simply switching the fluid exit stream between two, or more, positions while counter-flowing streams of liquids are provided to prevent sample contacting the sensing surfaces in advance of running the dispersed region to waste. The rise time in this design is simply a function of the volume of the flow cells. If connected in series, and using nL scale flow channels, then the sample rise/fall time may be reduced to <1 second at common flow rates. This greatly extends the range of rate constants that can be determined while also improving data quality in general. When samples are being injected, the flow of buffer input is no longer required and may be terminated. This will have no impact on the position of the adjacent fixed longitudinal laminar flows coming from the inlet ports off the opposite end of the sensing area.

Considering the nature of the sample fluid flow input in the present invention, the sample fluid composition and construction can be of any suitable type, as can the buffer or other fluid flow. In one type of sample flow construction, an air bubble may be included in the leading edge of the sample to lower dispersion before the sample is injected. Air bubbles form a physical barrier that prevents sample mixing with liquid contained in the flow injection system. This bubble separation method will decrease the volume of sample that must be discarded to waste before the injection proceeds. Such an air bubble is disposed in the sample flow at a position such that, in response to flows through open inlet ports and the initially open outlet port (with the other outlet closed), the air bubble passes into the sample inlet port and out the open outlet port without entering the portion of the flow channel having the sensing area, wherein the sample fluid after the position of the air bubble is suitable for injection across the sensing area in response to closing the initially open outlet port and opening the other outlet port. Of course, a sequence of such air bubble separated samples can be initially loaded and the present invention used to sequence them into the flow channel sensing area by alternating between the buffer and sample flows described above. Buffer flows are used to remove the air bubbles to waste outlets, and sample flows are used to move the respective sample into the flow channel. This eliminates the need for an autosampler, or other external loading to occur after the initial load into the loop communicating with the sample inlet port. This enables multiple injections to occur quickly one after another. The multiple loops (sample and buffer lines) can be used with different samples as well, and they can be interleaved between each other by switching back and forth between the loops.

The structures and methods described herein can be implemented in any suitable manner. There are known components, materials and manufacturing techniques known in the art with which to construct apparatus in accordance with the present invention. These can be operated in accordance with the descriptions herein to perform the methods of the present invention as well. Non-limiting examples of types of materials include relatively hard substances as stainless steel, glass, and PEEK, as well as compliant materials suitable for making sealing gaskets, provided such materials establish fluid sealed channels and ports, individually or in combination. Non-limiting examples of manufacturing techniques include molding, milling, stamping, and compressively adhering (such as between the two bodies described next).

With regard to a particular construction of flow cell, the present invention includes two structural bodies. One body includes a planar surface having the sensing area (whether with one or more sensing regions) disposed thereon. The other body includes a planar surface having a recessed microfluidic groove (one or more as needed) defined therein. The two bodies are connected with the recessed groove aligned with the sensing area, and the two planar surfaces are fluid tightly sealed together such that the fluid channel is a microfluidic channel defined between the aligned portions. Accordingly, it is apparent that from these planar surfaces the point of injection is coplanar with the sensing area in the channel, whereby the intersection where injection actually takes place is in the same plane as and immediately adjacent to the sensing area. That is, there is a flow junction or intersection where changes in the direction of both input streams allow alternation between sample loading and sample inject states, which junction or intersection is immediately adjacent to and coplanar with one or more sensing areas, with no access holes exposed between.

In a non-limiting example of such a structure, the fluidic channel has a rectangular cross section with a width in the range between 50 micrometers and 1 centimeter, a height in the range between 0.1 micrometer and 1 millimeter, and a length in the range between 10 micrometers and 1 centimeter. Other shapes and dimensions are within the scope of this invention. More generally, the flow channel volume between the injection point and the opposite waste port is within the range between 1 nanoliter and 1000 nanoliters (1 microliter). Additionally, the structure and method of the present invention are contemplated to work well with flow rates between 1 nanoliter/minute and 1000 microliters/minute during injection times between 1 second and 2 hours. Again, these are not limiting of broader aspects of the present invention.

Based on the description of the invention given above, the following are exemplary expressions or definitions of the methodology of the present invention.

The present invention includes a method for injecting, without significant dead volume, a fluid into a flow channel comprises flowing a first fluid and a second fluid in opposing first and second directions in the flow channel. These flows occur such that in the first direction the first fluid flows over a sensing area, from inlet access off a first end of the sensing area to outlet access off a second end of the sensing area, and removes, through outlet access off the second end of the sensing area, a dispersed portion of a second fluid entering the flow channel through inlet access off the second end of the sensing area. These flows also occur such that in the second direction second fluid subsequent to the dispersed portion thereof flows over the sensing area and removes the first fluid from the sensing area of the flow channel through outlet access off the first end of the sensing area. Flowing the first and second fluids includes intersecting the first and second fluid flows off the second end of the sensing area such that the intersection locus defines an injection entrance into the sensing area. Preferably the injection entrance is disposed less than 1 millimeter from the second end of the sensing area.

The present invention also includes a method for injecting a fluid into a biosensor flow cell comprises longitudinally flowing a buffer fluid along a conduit and sensing area from buffer port means to sample port means simultaneously with flowing sample fluid through the sample port means such that a dispersed portion of the sample fluid exits the biosensor flow cell without contacting ligands of the sensing area. This method further comprises thereafter longitudinally flowing the sample fluid through the conduit such that at least a portion of analyte of non-dispersed sample fluid contacts the ligands and the sample fluid pushes buffer fluid out through the buffer port means. Longitudinally flowing the various fluids occurs between various individual or combined fluid inputs and outputs. Examples include: flowing the buffer fluid from a buffer inlet of the buffer port means to a sample outlet of the sample port means; flowing the sample fluid from a sample inlet of the sample port means to a buffer outlet of the buffer port means; flowing the buffer fluid from a combined buffer inlet/outlet port of the buffer port means; and flowing the sample fluid from a combined sample inlet/outlet port of the sample port means. Various of these flows can be combined within particular implementations of the present invention.

The present invention also includes a method for injecting a fluid into a microfluidic test channel comprises flowing a buffer fluid, entering through a buffer port, longitudinally through a longitudinal conduit from one end of sensing areas to the other end of the sensing areas such that the buffer fluid flows over all the sensing areas. This method further comprises flowing a sample fluid, entering through a sample port, longitudinally through the longitudinal conduit from such other end of the sensing areas to the one end thereof such that the sample fluid flows over a fixed longitudinal path of the sensing areas. Flowing a sample fluid over a fixed longitudinal path includes flowing the sample fluid over the sensing areas which are disposed either in series or in parallel within the longitudinal conduit. The method can further comprise flowing a second sample fluid, entering through a second sample port communicating with the conduit off such other end of the longitudinally disposed sensing areas, longitudinally through the conduit from the second sample port to the one end of the sensing areas such that the second sample fluid flows over a fixed longitudinal path of the sensing areas adjacent to the fixed longitudinal path of the first-mentioned sample fluid. In one implementation, such multiple (i.e. two or more) sample flows can be effected by compartmentalizing the multiple flows of sample fluids adjacent their respective sample ports.

The present invention also includes a method for injecting fluids into a flow channel conduit system comprises reversibly controlling first and second longitudinal counter-flows along a sensing area through a flow channel. This includes controlling fluid flow through inlet and outlet ports for reversibly controlling the direction of flow over the sensing area by switching between a first outlet port and a second outlet port. This specifically includes: (1) opening a first inlet port, a second inlet port, and the second outlet port to provide simultaneous input flow through the first and second inlet ports and output flow through the second outlet port to discard a dispersed portion of a fluid entering through the open second inlet port, wherein in response to the open second outlet port and a closed first outlet port a sample fluid entering the second inlet port is made to flow to the second outlet port due to flow of a second fluid entering through the first inlet port; and (2) thereafter closing the second outlet port and opening the first outlet port to enable sample fluid injection over the sensing area as brought about by switching the outlet ports such that all flows are directed to the open first outlet port and away from the closed second outlet port, wherein the sample flow passes longitudinally along the length of the sensing area. In a particular implementation, reversibly controlling first and second longitudinal counter-flows includes, in response to closing the second outlet port and opening the first outlet port, injecting sample fluid at a flow rate within the range between 1 nanoliter/minute and 1,000 nanoliters/minute into the sensing area of the flow channel having a volume less than 1 microliter.

Example

A flow injection system was configured according to the invention as described in FIG. 2. The flow cell volume was approximately 30 nL. Water was flowed from inlet port 14 and exited the channel at waste port 20. Sample (i.e. 10% dimethylsulfoxide in water) was flowed from inlet port 16 and exited at waste port 20. In this configuration water was in contact with the sensing surface 28. The sensor response is plotted as a function of time (data rate of 10 Hz) in FIG. 11. During this period the dispersed (i.e. mixed) segment of the sample is allowed flow to waste port 20. Under our fluidic configuration at least 5 μL of sample was dispensed to waste before the sample was injected. The sensor response (which records the refractive index at the sensing surface 28) remains constant until the sample is injected. The injection over the sensing surface 28 was actuated by simultaneously opening waste port 18 and closing waste port 20. This causes an immediate reversal in the direction of fluid flow allowing the sample to contact the sensing surface 28. This is observed as a rapid increase in the sensor response followed by a plateau as the sample concentration over the sensing region approaches 100%. Returning the flow pattern to the original settings will cause a rapid wash out of sample over the sensing surface 28 and is observed as a rapid fall in the response. This sample injection procedure was repeated for different flow rates giving the response pattern in FIG. 11.

The rise and fall transition times were calculated as the 93% transition time in the experimental data (FIG. 11) and are shown in the following table.

| Flow Rate (μL/min) | Rise (s) | Fall (s) |
| --- | --- | --- |
| 100 | 0.06 | 0.06 |
| 80 | 0.06 | 0.08 |
| 60 | 0.08 | 0.09 |
| 40 | 0.09 | 0.13 |
| 20 | 0.13 | 0.26 |
| 10 | 0.21 | 0.59 |
| 5 | 0.37 | 0.93 |

The volume to be displaced for a 93% transition from water to sample, or sample to water, is only 82 nL (i.e. 2.72×30 nL). Given a flow rate of 5 μl/min (i.e. 83 nL/sec) we expect that the associated rise and fall times will be approximately 1 second. In practice the experimental fall time (i.e. 0.93 sec) is a reasonable approximation of the expected fall time. However, the rise time (i.e. 0.37 sec) is 2.7 fold faster than expected. This might suggest that the rise time is obeying a linear, as opposed to exponential, displacement of the flow cell volume. However, such an accelerated rise time may be better explained by the existence of a transient pulse in the flow rate. This momentary increase in flow rate at the time of flow reversal is induced by the decay of a small pressure difference between the two flow paths. After the pressure decays the flow rate approximates the set point flow rate within a time that is in the order of the rise/fall time. Therefore, this transient pressure decay may also be exploited to accelerate rise/fall times.

As an alternative, one could have both waste ports open at the same time and use relative flow rates to control the transitioning or switching. Variable control could be implemented by changing flow rates from low for one flow, high for the other, to high for the first and low for the second, and rates in between. These rates can be varied relative to each other to obtain split flows as well as "all or nothing" flows (all of one, none of another).

As used in this document, "comprising" and "including" do not limit the statement to only those particular items listed.

Thus, the present invention is well adapted to carry out the objects and attain the ends and advantages mentioned above as well as those inherent therein. While preferred embodiments of the invention have been described for the purpose of this disclosure, changes in construction and arrangement of parts and the performance of steps can be made by those skilled in the art, which changes are encompassed within the spirit of this invention as defined by claims as they are appended.

What is claimed is:

1. A flow cell, comprising:
    a longitudinal flow channel conduit having a first sensing area defined therein;
    a first inlet port providing an entrance of a first fluid into the flow channel conduit;
    a second inlet port providing an entrance of a second fluid into the flow channel conduit;
    a first outlet port providing a first exit for the first and second fluids out of the flow channel conduit;
    a second outlet port providing a second exit for the first and second fluids out of the flow channel conduit, wherein the first and second inlet ports are positioned between the first and second outlet ports, wherein the first sensing region is positioned between the first and second inlet ports, and wherein the first sensing region is in longitudinal alignment with the first and second inlet ports and the first and second outlet ports; and
    an outlet selector valve for selectively opening and closing the first and second outlet ports.

2. A flow cell as defined in claim 1, further comprising:
    means for controlling the flow rate of the first fluid; and
    means for controlling the flow rate of the second fluid.

3. A flow cell as defined in claim 1, further comprising a second sensing area and a third sensing area, wherein the second and third sensing areas are positioned parallel to the first sensing area within the longitudinal flow channel conduit, and wherein the first sensing area is positioned between the second and third sensing areas.

4. A flow cell as defined in claim 1, wherein if the outlet selector valve is selected to open the second outlet port, then the first outlet port is closed such that when the first fluid and second fluid are present in the flow channel conduit, the first fluid is caused to flow in a first direction from the first inlet port over the sensing region to the second outlet port and the second fluid is caused to flow in the first direction from the second inlet port to the second outlet port, and wherein if the outlet selector valve is selected to open the first outlet port, then the second outlet port is closed thereby causing the first fluid to flow in a second direction from the first inlet port to the first outlet port and the second fluid to flow in the second direction from the second inlet port over the sensing region to the first outlet port.

5. A flow cell as defined in claim 3 further comprising:
    a third inlet port providing an entrance of a third fluid into the flow channel conduit;
    a fourth inlet port providing an entrance of a fourth fluid into the flow channel conduit;
    a third outlet port providing a third exit for the first and third fluids out of the flow channel conduit;
    a fourth outlet port providing a fourth exit for the first and fourth fluids out of the flow channel conduit;
    wherein the second sensing region is in longitudinal alignment with the third inlet port and third outlet port, wherein the third sensing region is in longitudinal alignment with the fourth inlet port and fourth outlet port, wherein the second inlet port is positioned between the third inlet port and fourth inlet port, and wherein the second outlet port is positioned between the third outlet port and fourth outlet port.

* * * * *